(12) United States Patent
Reuteler

(10) Patent No.: US 9,151,770 B2
(45) Date of Patent: Oct. 6, 2015

(54) STORAGE STACKS

(75) Inventor: Beat Reuteler, Bützberg (CH)

(73) Assignee: Brooks Automation, Inc., Chelmsford, MA (US)

( * ) Notice: Subject to any disclaimer, the term of this patent is extended or adjusted under 35 U.S.C. 154(b) by 444 days.

(21) Appl. No.: 13/501,880

(22) PCT Filed: Oct. 18, 2010

(86) PCT No.: PCT/EP2010/065656
§ 371 (c)(1),
(2), (4) Date: Jun. 13, 2012

(87) PCT Pub. No.: WO2011/048058
PCT Pub. Date: Apr. 28, 2011

(65) Prior Publication Data
US 2012/0272500 A1    Nov. 1, 2012

(30) Foreign Application Priority Data
Oct. 19, 2009    (WO) .................. PCT/EP2009/063684

(51) Int. Cl.
*G01N 35/10*    (2006.01)
*G01N 35/00*    (2006.01)

(52) U.S. Cl.
CPC ........ *G01N 35/1095* (2013.01); *G01N 35/0099* (2013.01); *G01N 2035/00326* (2013.01); *G01N 2035/00435* (2013.01); *G01N 2035/00445* (2013.01); *Y10T 29/49826* (2015.01)

(58) Field of Classification Search
USPC ........... 62/266, 382, 265, 378, 336, 337, 331; 312/312; 422/63; 198/468.8; 29/434, 29/455.1, 469
See application file for complete search history.

(56) References Cited

U.S. PATENT DOCUMENTS 2,077,739 A * 4/1937 Bryant ............................. 62/379
2,165,513 A * 7/1939 Smith .............................. 62/302
(Continued)

FOREIGN PATENT DOCUMENTS

EP    0904841 A2    3/1999
EP    0925333 A1    6/1999
(Continued)

OTHER PUBLICATIONS

International Search Report dated Jan. 25, 2011.
(Continued)

*Primary Examiner* — Essama Omgba
(74) *Attorney, Agent, or Firm* — Perman & Green, LLP; Colin C. Durham

(57) ABSTRACT

A storage stack for storing sample containers in a low temperature sample store, each storage stack includes first and second rigid lateral support flanges including a multitude of storage webs for supporting sample containers; a rigid back panel; a rigid bottom plate; and a rigid insulation cover. The insulation cover includes a handling plate and an insulation block. A number of insulation covers of all storage stacks of a storage stack array form an essentially continuous insulation layer on a storage area of the low temperature sample store. For all storage stacks, carrying elements are provided that statically connect the bottom plate of each individual storage stack with a bottom structure of the storage area, carry the entire weight of the individual storage stack and all sample containers inserted therein, and confer this entire weight to a bottom structure of the storage area of the low temperature sample store.

20 Claims, 5 Drawing Sheets

(56) References Cited

U.S. PATENT DOCUMENTS

| | | | | |
|---|---|---|---|---|
| 2,490,694 | A * | 12/1949 | Leutheuser | 312/408 |
| 4,969,336 | A * | 11/1990 | Knippscheer et al. | 62/266 |
| 5,233,844 | A * | 8/1993 | Knippscheer et al. | 62/440 |
| 5,690,892 | A * | 11/1997 | Babler et al. | 422/63 |
| 5,921,102 | A * | 7/1999 | Vago | 62/337 |
| 6,065,294 | A * | 5/2000 | Hammerstedt et al. | 62/3.3 |
| 6,082,417 | A * | 7/2000 | Horn | 141/130 |
| 6,357,983 | B1 | 3/2002 | Junca | |
| 6,564,120 | B1 * | 5/2003 | Richard et al. | 700/214 |
| 6,637,473 | B2 * | 10/2003 | Ganz et al. | 141/130 |
| 6,694,767 | B2 | 2/2004 | Junca | |
| 6,974,294 | B2 * | 12/2005 | Pressman et al. | 414/331.03 |
| 7,352,889 | B2 * | 4/2008 | Ganz et al. | 382/141 |
| 7,635,246 | B2 * | 12/2009 | Neeper et al. | 414/280 |
| 7,648,321 | B2 * | 1/2010 | Neeper et al. | 414/281 |
| 8,083,994 | B2 * | 12/2011 | Neeper et al. | 422/65 |
| 8,252,232 | B2 * | 8/2012 | Neeper et al. | 422/65 |
| 8,371,132 | B2 * | 2/2013 | Cutting et al. | 62/66 |
| 8,448,457 | B2 * | 5/2013 | Cutting et al. | 62/66 |
| 8,857,208 | B2 * | 10/2014 | Malin | 62/440 |
| 2003/0185657 | A1 * | 10/2003 | Stefani | 414/281 |
| 2003/0233842 | A1 * | 12/2003 | Junca et al. | 62/266 |
| 2004/0037680 | A1 * | 2/2004 | Sato et al. | 414/281 |
| 2004/0141882 | A1 | 7/2004 | Mimura et al. | |
| 2004/0144593 | A1 * | 7/2004 | Shai | 182/141 |
| 2005/0026295 | A1 * | 2/2005 | Harding et al. | 436/43 |
| 2005/0279182 | A1 * | 12/2005 | Cole et al. | 73/864.71 |
| 2006/0006774 | A1 * | 1/2006 | Jackson et al. | 312/350 |
| 2006/0045674 | A1 * | 3/2006 | Craven | 414/277 |
| 2006/0053825 | A1 * | 3/2006 | Owen et al. | 62/441 |
| 2007/0172396 | A1 * | 7/2007 | Neeper et al. | 422/104 |
| 2008/0213080 | A1 * | 9/2008 | Cachelin et al. | 414/791.6 |

FOREIGN PATENT DOCUMENTS

| | | |
|---|---|---|
| EP | 1391402 A2 | 2/2004 |
| EP | 1895307 A1 | 3/2008 |
| EP | 1939561 A2 | 7/2008 |
| EP | 1975626 A1 | 10/2008 |
| FR | 2888328 A1 | 1/2007 |
| JP | 2004131249 A | 4/2004 |

OTHER PUBLICATIONS

International Search Report dated Jul. 6, 2010.
International Preliminary Report on Patentability Application PCT/EP2010/065656 dated Apr. 24, 2012.
International Preliminary Report on Patentability Application PCT/EP2009/063684 dated Mar. 26, 2012.

* cited by examiner

Fig. 6
Fig. 7
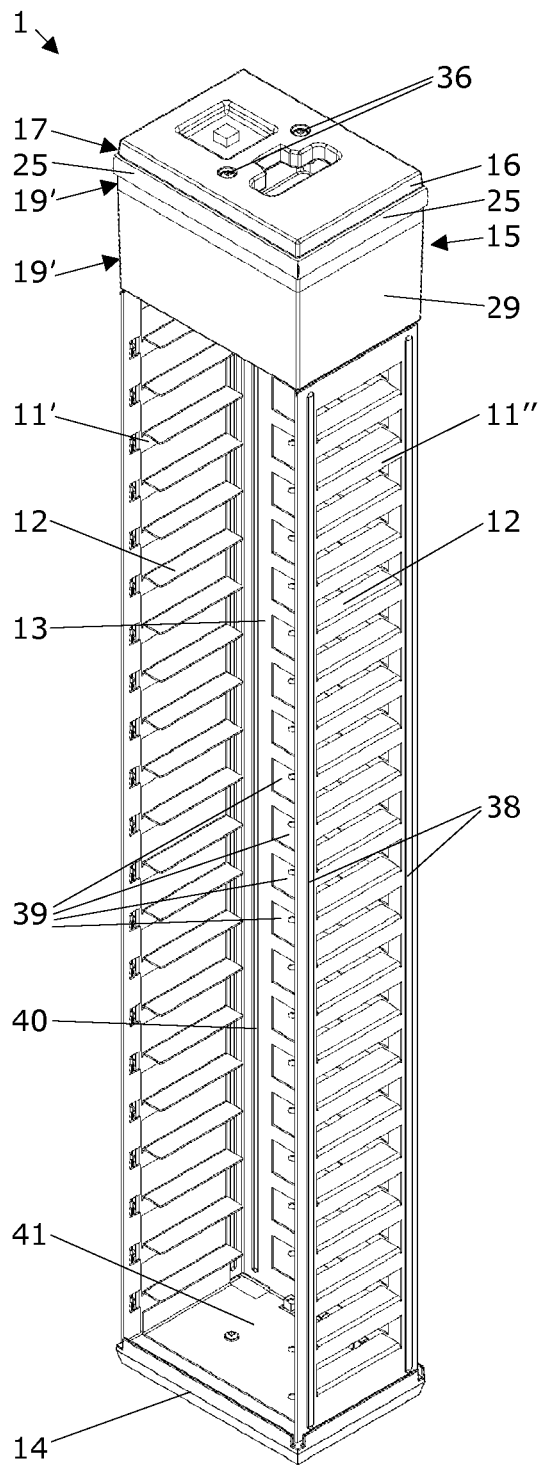
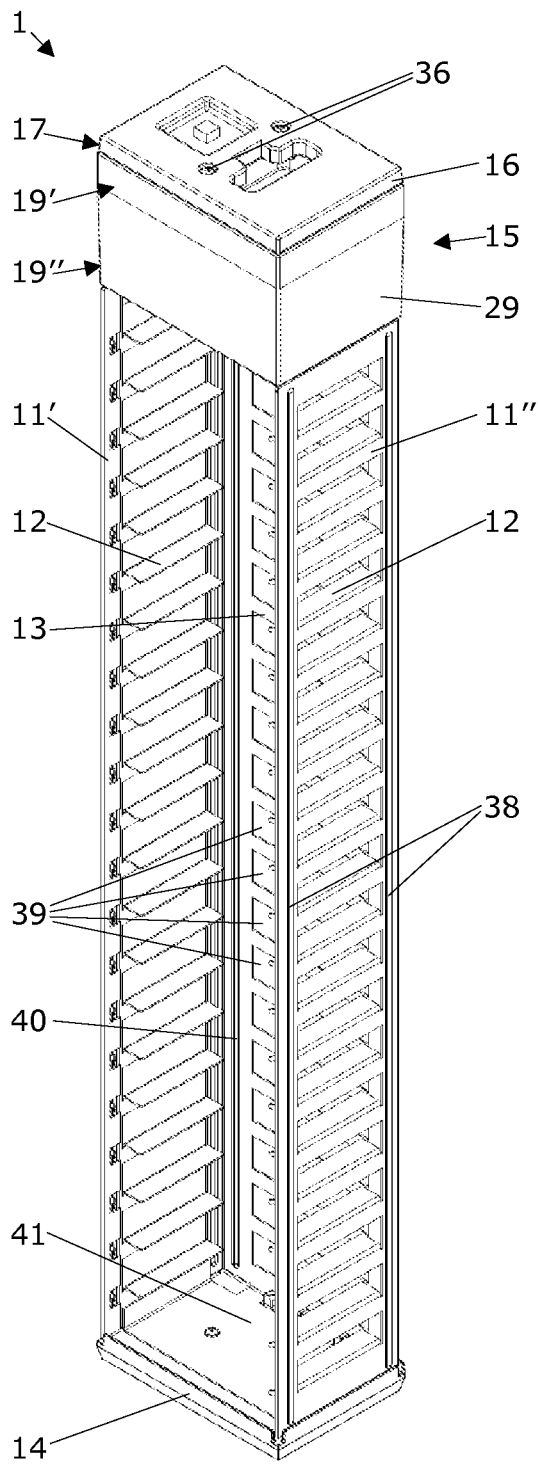

STORAGE STACKS

CROSS-REFERENCE TO RELATED APPLICATIONS

This application is the National Stage of International Application No. PCT/EP2010/065656 International Filing Date 18 Oct. 2010, which designated the United States of America, and which International Application was published under PCT Article 21 (s) as WO Publication No. WO2011/048058 A1 and which claims priority from, and the benefit of, international Application No. PCT/EP2009/063684 filed on 19 Oct. 2009, the disclosures of which are incorporated by reference in their entireties.

BACKGROUND

1. Field

The aspects of the disclosed embodiment refer to storage stacks for a modular sample store for storing biological, chemical and/or biochemical samples. More particularly, this application refers to storage stacks comprising particular insulation covers for use in a temperature controlled modular sample store for storing such samples at controlled temperature conditions, preferably in the range of −25° C. to −90° C. In the preferred embodiment, this application refers to a storage stack for storing sample containers in a low temperature sample store. Such a low temperature sample store is equipped with a robot that is capable to acting according to Cartesian X, Y, and Z coordinates for horizontally positioning sample containers in X/Y planes inside of individual storage stacks. The robot is also capable to vertically moving individual storage stacks within the low temperature sample store in Z direction between a bottom storage position and elevated access positions. The sample store typically defines a storage area for accommodating an array of such storage stacks. This storage area preferably comprises a number of first lattice constants of an orthogonal lattice in the horizontal X direction and a number of second lattice constants of said orthogonal lattice in the horizontal Y direction. The total number of storage stacks of the storage stack array is accomplished to be oriented adjacent to each other and parallel to the vertical Z direction.

2. Brief Description of Related Developments

Biological samples, such as body fluids (e.g. blood, urine, sputum or sperm), cells (e.g. bacterial cell cultures), or tissue samples (e.g. taken from human, animals or plants) are extremely temperature sensitive and have to be cooled or frozen immediately after taking the samples in order to prevent their destruction. Thus, an important aspect during investigation of biological samples and temperature sensitive samples in general is storage and provision of these samples in frozen state, i.e. at low temperatures. Storage and provision can be done in commercially available freezers (i.e. at temperatures of at most −18° C.), in a gas atmosphere that is cooled by dry ice (i.e. solid C02) to −78.5° C., or in liquid nitrogen (at −196° C.). In addition, freezers operating with compressors are known which provide storage temperatures of −35° C. (single-stage), −85° C. (double-stage), or −135° C. (triple-stage).

All these storage procedures and apparatuses are well known, but also provide certain drawbacks. Samples stored at a temperature of −18° C. can exhibit destruction artifacts already after short storage terms because of growing ice crystals. Such ice crystal growth is considerably reduced at dry ice temperatures and essentially does not take place in liquid nitrogen. However on the one hand, dry ice cooled containers warm up relatively fast as soon as all of the C02 has sublimated. On the other hand, storage in liquid nitrogen is cumbersome and only possible with dedicated safety measures and appropriately educated personal. Especially for robotic or automated storage and withdrawal/provision of a large number of samples there exist only very few of the known systems. Chemical samples (e.g. prepared reagent aliquots of defined concentration) and biochemical samples (e.g. concentrated and purified enzymes) are known to be stored more and more in automatic storage systems for large laboratories with the task of being provided and accessible at any time. In so called "large stores" or "bio-banks", storage temperatures of about −20° C. for chemical samples and of about −80° C. for biological and biochemical samples have proven to be reasonable.

From the U.S. Pat. No. 6,357,983 B1, an automatic storage system is known. In a conditioned chamber, the temperature of which being selectable in a range from −20° C. to +20° C., there are located two ring-like, nested shelves, which are rotatable around a common central axis, and which comprise a large number of horizontally orientated, superimposed shelf board positions. These shelf board positions can be accessed by a robot that moves vertically and outside of the shelves. This robot is equipped with an especially articulated gripper mechanism in order to reach to an inner shelf board position by penetrating an adjacent outer shelf board position. This system has the advantage that the robot, and thereby the sample, are located within the cold atmosphere during the entire process of selecting the sample. However, this system seems to be rather limited in the number of shelf boards, which results in cooling down a relatively large volume that can take up only a quite small number of samples. Moreover, a rather complex robot mechanism has to be utilized.

Another storage system for storing and providing frozen samples is known from the patent application EP 1 939 561 A2. This document discloses a compact storage system and a related method for storing frozen samples in such a compact storage system, which comprises a storage area within a thermally insulated housing that is equipped with a cooling device for cooling the storage area to at least −15° C. This compact storage system comprises revolving storage shelves in the form of a paternoster that are arranged entirely within the cooled storage area. This compact storage system also comprises a transfer area that is located above said storage area, a robot being moveable in essentially horizontal directions within this transfer area. The robot is accomplished to load a storage shelf into or to remove a storage shelf from the uppermost position of the upper half circle of the revolving storage shelves. The robot can also take out from a storage shelf or insert a single object into a storage shelf that is located at this vertex position of the paternoster. The storage area of this system appears to be quite compact. However, the mechanics of the paternoster have to be moved at temperatures down to −80° C.; because of the danger of frost condensation and thereby blocking the mechanics of the paternoster, elaborate and expensive measures are believed to be essential.

Other storage systems of the company REMP AG (Oberdiessbach, Switzerland) are known, in which samples are stored at +4° C. or −20° C. (REMP Small-Size Store™), or in which samples are stored at −80° C. (REMP Bio-Sample Store). In the latter, a robot is implemented that is fully operable at −20° C.

Again another storage system is known from the U.S. Pat. No. 6,694,767 B2. Below a working area with controlled atmosphere, in which a robot with workplace is arranged, is located a thermally completely insulated storage space that is accomplished for storage temperatures of −85° C. to −80° C.

Storage shelves with relatively small horizontal dimensions and numerous shelf boards superimposed to each other are vertically suspended in openings of the thermally insulating ceiling plate of the storage area. The storage shelves comprise an upper cover, that carries the storage shelf and that overlaps and closes the opening in the thermally insulating ceiling plate in which the storage shelve is completely inserted. Such closing of the access opening for inserting a storage shelf is always carried out under the effect of gravity, i.e. in their down-most storage position, the storage shelves actually hang with their upper cover at the thermally insulating ceiling plate. A robot lifts such a storage shelf out of the storage area in order to allow accessing a particular shelf board by an appropriate tool for removing a sample container from that shelf board of for depositing a sample container on that shelf board.

BRIEF DESCRIPTION OF THE DRAWINGS

The storage stack according to the disclosed embodiment is now described in detail with the help of drawings that point to aspects of the disclosed embodiments without limiting the scope of the disclosed embodiment.

FIG. 4A shows detailed vertical partial sections of a storage stack according to a first variant of the rigid insulation cover that comprises a resilient circumferential seal, wherein:

FIG. 6 shows a 3D view of an entire storage stack according to a first variant of the insulation cover that comprises a resilient circumferential seal;

FIG. 7 shows a 3D view of an entire storage stack according to a second variant of the insulation cover that defines sealing gaps;

DETAILED DESCRIPTION

Figure 1:
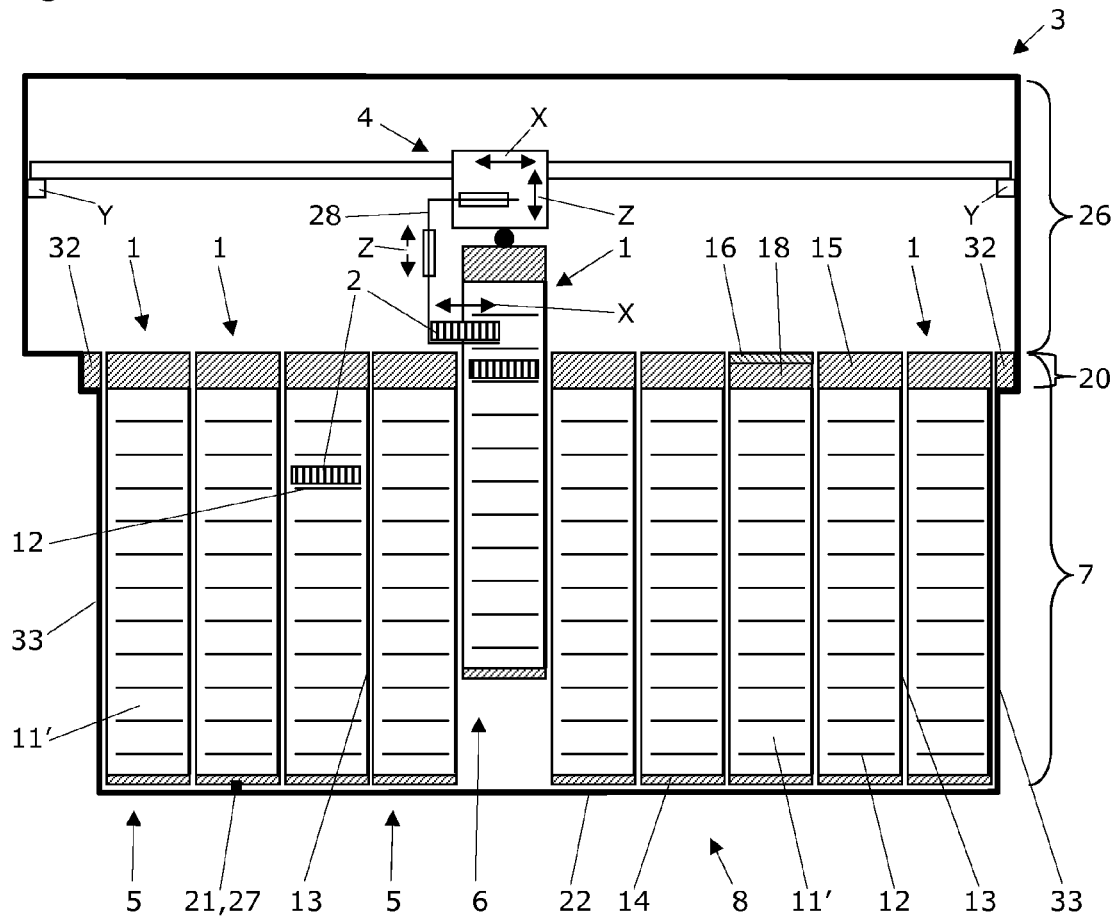
FIG. 1 is a schematic vertical section through a low temperature sample store that is equipped with an array of storage stacks according to the invention.

FIG. 1 shows a schematic vertical section through a low temperature sample store 3 that is equipped with an array 8 of storage stacks 1 according to the invention. The storage stack according to the invention 1 is accomplished for storing sample containers 2 in a low temperature sample store 3.

In the context with the disclosed embodiment, the term "sample container" is to be understood as a standard multi-well microplate according to the ANSI/SBS standards 1-2004 and 2-2004 or a multi-well microplate with comparable dimensions. The term "sample container" is also to be understood as a rack for inserting micro-tubes as e.g. published in EP 0 904 841 B1; such racks preferably have similar or identical dimensions as standard microplates. Further, the term "sample container" is to be understood as a cell culture flask that preferably has similar dimensions as a standard microplate and that can be stored in an essentially horizontal position. A blood bag is another "sample container" in the context with the disclosed embodiment; such blood bags could be supported by a tray that has about the same footprint like a standard microplate.

The low temperature sample store 3 typically is equipped with a robot 4. The robot 4 preferably is acting according to Cartesian X, Y, and Z coordinates for horizontally positioning sample containers 2 in X/Y planes inside of individual storage stacks 1 (indicated in each case with double arrows). Small deviations from precise horizontal positioning of the sample containers 2 inside the storage stack 1 can be neglected as long as the sample containers 2 do not autonomously slide out of the storage rack 1 during vertical movements of the latter.

Such vertical movements of individual storage stacks 1 within the low temperature sample store 3 in Z direction are carried out by the robot 4. These vertical movements are carried out between a bottom storage position 5 and elevated access positions 6 of the storage stacks 1. Except for one storage rack 1, all storage racks are depicted at their lower-most position, the bottom storage position 5 within the storage area 7 of the low temperature sample store 3. One of the storage stacks 1 is lifted by the robot 4 to a certain elevated access position 6, where an extendable arm 28 (indicated with separated double arrows) of the robot 4 is loading or unloading a sample container 2 from the storage stack 1.

The sample store 3 defines a storage area 7 for accommodating an array 8 of storage stacks 1. The storage area 7 comprises m first lattice constants 9 of an orthogonal lattice in the horizontal X direction and n second lattice constants 10 of said orthogonal lattice in the horizontal Y direction (see FIG. 2). The m×n storage stacks 1 of the storage stack array 8 are accomplished to be oriented adjacent to each other and parallel to the vertical Z direction. The storage area of the low temperature sample store 3 comprises a surrounding rim 32 that exhibits the same materials and geometry to the adjacent storage stacks 1. The surrounding rim 32 has a distance to the adjacent storage stacks that preferably is identical with the width of gap 23 between all the storage stacks 1. This measure is preferred for providing all storage stacks 1 in the storage area 7 practically the same surrounding.

According to aspects of the disclosed embodiment, each storage stack 1 for storing sample containers 2 in a low temperature sample store 3 comprises first and second rigid lateral support flanges 11',11" that extend in the Z direction and that comprise a multitude of storage webs 12 for supporting sample containers 2 inserted into the storage stack 1. These storage webs 12 are subsequently grouped in the Z direction in mutual pairs that protrude about the lateral support flanges 11',11" and that are located thereon on the same Z-level (compare FIGS. 6 and 7).

According to aspects of the disclosed embodiment, each storage stack 1 for storing sample containers 2 in a low temperature sample store 3 comprises a rigid back panel 13, rigidly linking the lateral support flanges 11',11" to each other (compare FIGS. 4 and 5).

Figure 4A:
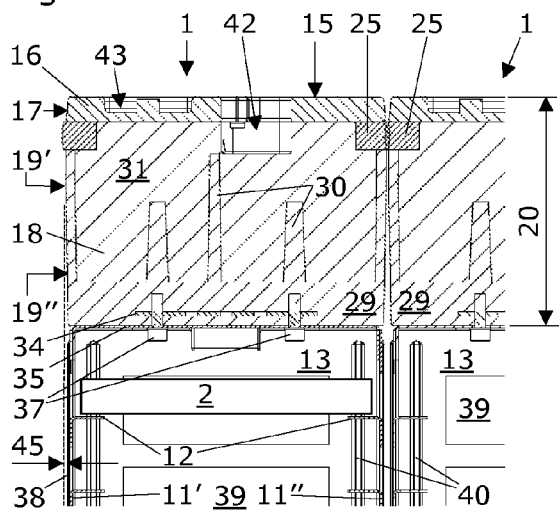
Figure 5A:
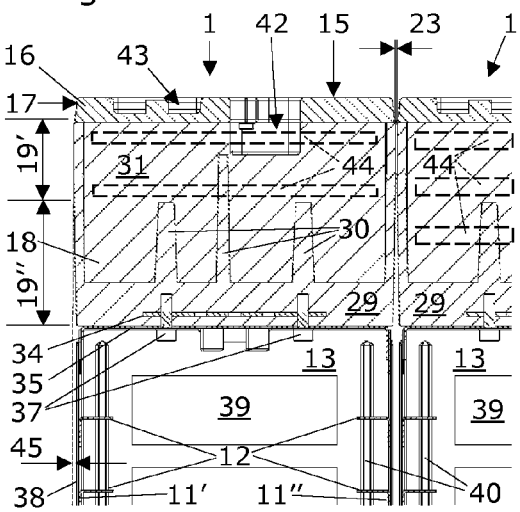
FIG. 5A shows detailed vertical partial sections of a storage stack according to a second variant of the rigid insulation cover that defines sealing gaps.
Figure 4B:
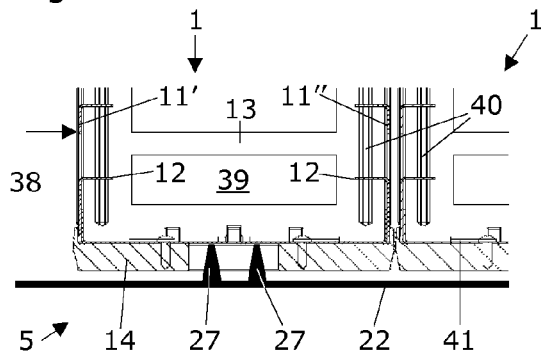
FIG. 4B shows the rigid bottom plate of the storage stack of FIG. 4A and carrying pins that are attached to the bottom structure of the storage area of the low temperature sample store.
Figure 5B:
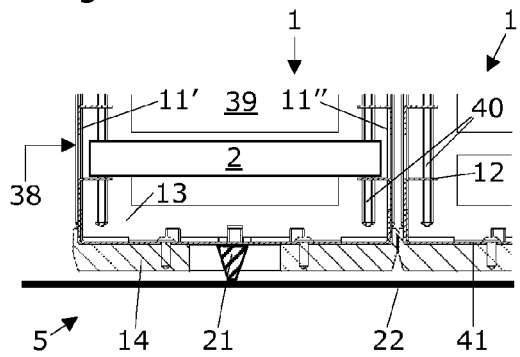
FIG. 5B shows the rigid bottom plate of the storage stack of FIG. 5A and a trunnion that is attached to the rigid bottom plate of the storage stack.

According to aspects of the disclosed embodiment, each storage stack 1 for storing sample containers 2 in a low temperature sample store 3 comprises a rigid bottom plate 14 that is fixed to lower ends of at least one lateral support flange 11',11" and/or of the back panel 13 (compare FIGS. 4B and 5B).

According to aspects of the disclosed embodiment, each storage stack 1 for storing sample containers 2 in a low temperature sample store 3 comprises a rigid insulation cover 15 that is fixed to upper ends of at least one lateral support flange 11',11" and/or of the back panel 13. This insulation cover 15 comprises a handling plate 16 with a plate circumference surface 17, and an insulation block 18 with a block circumference surface 19 (compare FIGS. 4A and 5A). The m×n insulation covers 15 of all storage stacks 1 of the storage stack array 8 form an essentially continuous insulation layer 20 on the storage area 7 of the low temperature sample store 3 (see FIGS. 1 and 2).

The storage stacks 1 of the disclosed embodiment particularly are characterized in that carrying elements 21,27 are provided. These carrying elements 21,27 statically connect the bottom plate 14 of each individual storage stack 1 with a bottom structure 22 of the storage area 7 of the low temperature sample store 3. These carrying elements 21,27 are accomplished to carry the entire weight of the individual storage stack 1 and all sample containers 2 inserted in this storage stack 1 and to confer this entire weight to the bottom structure 22 of the storage area 7 of the low temperature sample store 3.

In FIG. 1 it is shown that the transfer area 26 of the low temperature sample store 3 preferably is wider than the storage are 7. This is particularly useful for being able to insert a sample container 2 in the leftmost row of storage stacks. It is further shown that the storage stacks 1 abut with their bottom plates 14 the bottom structure 22 of the storage area 7 of the low temperature sample store 3. This is not favored however, because there exists the danger of freezing the bottom plates 14 to the bottom structure 22 of the storage area 7; such freezing could disadvantageously immobilize the storage stacks 1 or at least constrict free vertical movement of the storage stacks 1. It is thus preferred to minimize the contact surface between the storage stacks 1 and the bottom structure 22.

According to a first aspect, the carrying element of an individual storage stack 1 is accomplished as one or more trunnions 21 (compare with FIG. 5B). These trunnions 21 are attached to the rigid bottom plate 14 of the storage stack 1 and abut the bottom structure 22 of the storage area 7 of the low temperature sample store 3 when the individual storage stack 1 is in its bottom storage position 5.

According to a second aspect, the carrying element of an individual storage stack 1 is accomplished as one or more carrying pins 27, said carrying pins 27 being attached to the bottom structure 22 of the storage area 7 of the low temperature sample store 3 and are abutted by the bottom plate 14 of an individual storage stack 1 when this is lowered to its bottom storage position 5.

Figure 2:
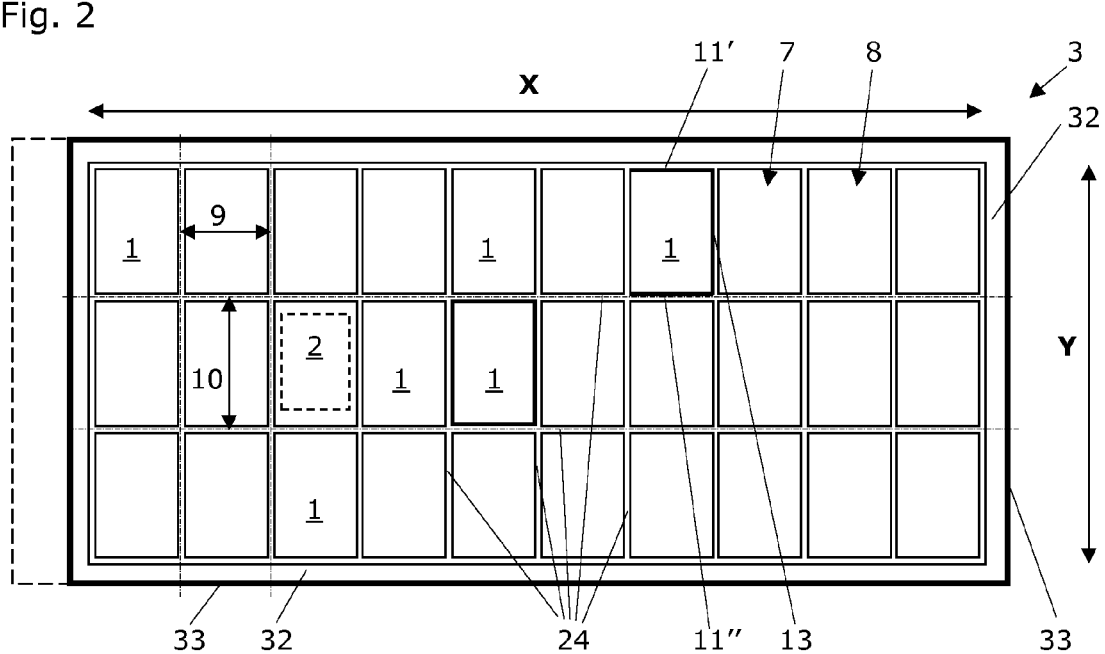
FIG. 2 is a schematic ground view of the low temperature sample store of FIG. 1 that is equipped with an array of storage stacks according to the invention.

FIG. 2 shows a schematic ground view of the low temperature sample store 3 of FIG. 1 that is equipped with an array 8 of storage stacks 1 according to the invention. The smaller first lattice constant 9 is pointing into the X direction and the larger second lattice constant 10 is pointing into the Y direction. This FIG. 2 shows an exemplary array of 10×3 storage stacks 1, one of which is in an elevated access position. The preferred storage stack array 8 counts 12×10 storage stacks with the following preferred specification of a storage stack 1 as shown in Table 1.

TABLE 1

|  | Height [mm] | Length [mm] | Width [mm] | Material |
|---|---|---|---|---|
| Storage stack | 795 | — | — | — |
| Insulation cover | 100 | 140.5 | 98 | hd/ld PU |
| Handling plate | 11 | 140 | 98 | hd PU |
| Insulation block | 89 | 140.5 | 98 | hd/ld PU |
| Support flange/ back panel combination | 683 (incl. 7 mm insert into bottom plate) | 137 | 94 | Al |
| Bottom plate | 19 | 141 | 98.5 | hd PU |

Wherein hd means high density, ld means low density, PU means polyurethane, and Al means aluminum or an aluminum alloy.

The number of pairs of storage webs 12 depends very much on the height of the sample containers that are to be inserted into the storage stacks 1. Given the specification of storage stack 1 as shown in table 1, the pairs of storage webs on the lateral support flanges 11',11" have a distance to e.g. take up 12 plates STBR 96-900, 21 plates STBR 96-300, or 26 plates STBR 384. Other formats and plates with nanotubes or cryotubes are possible as well as long as they exhibit a foot print that essentially is the foot print of a standard microplate.

Figure 3A:
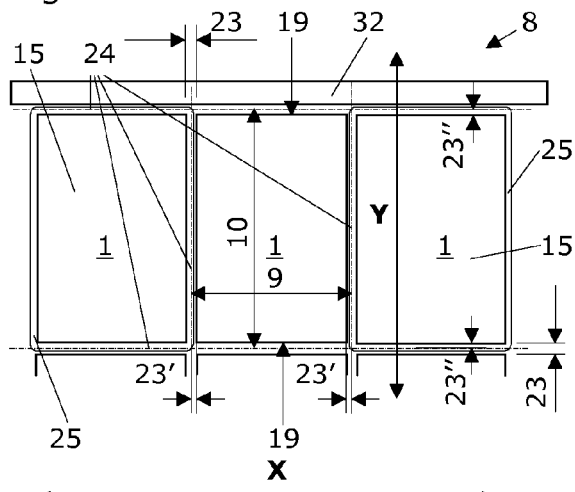
FIG. 3A shows the relative sizes of resilient circumferential seals and gaps with respect to the insulation covers.

FIG. 3A shows enlarged details of FIG. 2. In particular, FIG. 3A shows the relative sizes of resilient circumferential seals 25 and gaps 23 with respect to the insulation covers 15 of the storage stacks 1. It is clear from this FIG. 3A that the lattice axes of the storage stack array 8 run in the middle of the gap 23 between the insulation covers 15 of the storage stacks 1. The first and second gap parts 23',23" correspond to the distances of the block circumference surfaces 19 to the lattice axes of the storage stack array 8 and sum up to the gaps 23. It is also clear from this FIG. 3A that the resilient circumferential seals 25 extend beyond the lattice axes of the storage stack array 8. The gap parts 23',23" form a gap array 24 that is coincident with said orthogonal lattice.

Based on a first variant of the insulation cover 15 of the inventive storage stack 1, a gap 23 between the insulation covers 15 always is present. This is true in the event that all storage racks 1 are at their bottom storage position 5 inside a low temperature sample store 3. This is also true in the event that at least one of the storage stacks 1 inside a low temperature sample store 3 is lifted to an elevated access position 6. However, the size or width of the gap turned out to be absolutely crucial, because on the one hand, the air in the storage area 7 of the low temperature sample store 3 (typically at a temperature of −60° C. to −90° C.) tends to penetrate through the gaps 23 or the entire gap array 24. On the other hand, the air in the transfer area 26 of the low temperature sample store (typically at a temperature of −10° C. to −40° C.) tends to penetrate through the gaps 23 or the entire gap array 24 as well. Such exchange and mixture of the air preferably is to be hindered to the most reasonable extent in order to keep the low temperature inside the storage area 7 of the low temperature sample store 3. Furthermore, such exchange and mixture of the air preferably is to be hindered to the most reasonable extent in order to minimize water vapor insertion into the storage area 7 of the low temperature sample store 3.

Because of this findings, the handling plate 16 and the insulation block 18 of the insulation cover 15 have a horizontal overall extension in the X and Y direction that is greater than 95%, preferably greater than 97%, of the first and second lattice constants 9,10 of said orthogonal lattice. It is most preferred however that the handling plate 16 and the insulation block 18 of the insulation cover 15 have a horizontal overall extension in the X and Y direction that is equal or greater than 99% of the first and second lattice constants 9,10 of said orthogonal lattice.

Preferably, the handling plate 16 and the insulation block 18 of the insulation cover 15 have a horizontal overall extension in the X direction that is less than 2% smaller than the first lattice constant 9 and that is less than 1.4% smaller than the second lattice constant 10 in the Y direction of said orthogonal lattice. It is even more preferred that the handling plate 16 and the insulation block 18 of the insulation cover 15 have a horizontal overall extension in the X direction that is 1% smaller than the first lattice constant 9 and that is 0.7% smaller than the second lattice constant 10 in the Y direction of said orthogonal lattice.

It is further preferred that the handling plate 16 and the insulation block 18 of the insulation cover 15 define first gap parts 23' of 0.5% of the first lattice constant 9 in the X direction and second gap parts 23" of 0.35% of the second lattice constant 10 in the Y direction of said orthogonal lattice.

In practice, the most preferred width of the gap 23 is 1 mm. This said, it is to be noted that of high importance as well is the path length of the gap 23, i.e. the dimension of the gap 23 in the Z direction. Given the total height of the insulation cover 15 to be 100 mm (see table 1), the path length of the gap preferably is 75 mm (see FIG. 9). Over the entire height of this gap 23, the vertical block circumference surface 19' runs parallel to the vertical axis Z. There is however always preferred that an inclined block circumference surface 19" is present in the high density polyurethane shell 29 of the rigid insulation cover 15. This inclined block circumference surface 19" has thus a cone-like outer surface that provides a self-centering and guiding function when lowering the storage stack to its bottom storage position 5.

Based on a second variant of the insulation cover 15 of the inventive storage stack 1, a gap 23 between the insulation covers 15 is not present, because the insulation cover 15 comprises a circumferential resilient seal 25. This circumferential resilient seal 25 is depicted in FIG. 3A and protrudes about the block circumference surface 19 of the insulation block 18 to an extent that is more than the first and second gap parts 23',23". In other words, the circumferential resilient seal 25 needs to be partially compressed in order to assume a protruding dimension that is equal to the first and second gap parts 23',23" and that is sufficient to close the gap together with the circumferential resilient seal 25 of the adjacent storage stack 1.

Because of these findings, the insulation cover 15 of the storage stack 1 preferably comprises a resilient circumferential seal 25 that partially is located between the handling plate 16 and the insulation block 18 and that partially protrudes on all sides beyond the circumference surfaces 17,19 of the handling plate 16 and insulation block 18. The extent of protrusion preferably is such that the circumferential seal 25 extends beyond the first lattice constant 9 in the X direction and beyond the second lattice constant 10 in the Y direction of said orthogonal lattice. Preferably the resilient circumferential seal 25 of a single storage stack 1 protrudes about more than 0.2% beyond the lattice constants 9,10 in the X direction and in the Y direction of said orthogonal lattice.

In practice and based on the dimensions as indicated in table 1, the resilient circumferential seal 25 of a single storage stack 1 protrudes at +25° C. about 0.75% and at −80° C. about 0.35% beyond the lattice constants 9,10 in the X direction and in the Y direction of said orthogonal lattice. This resilient circumferential seal 25 is made of resilient polyethylene foam that exhibits creeping at temperatures at least down to a temperature of −80° C. This resilient circumferential seal 25 for each sin-gle storage stack 1 has a height of 15 mm, but is compressed to a height of 12 mm by the placement between the handling plate 16 and the insulation block 18 of the insulating cover 15.

Figure 3B:
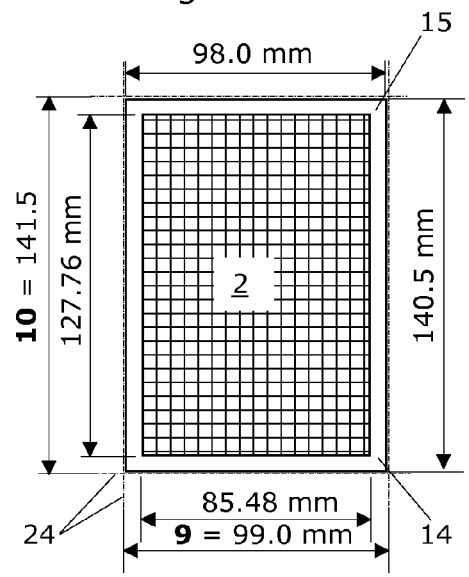
FIG. 3B shows the actual horizontal dimensions of a preferred embodiment of the storage stack, storage stack array, and microplate.

FIG. 3B shows the actual horizontal dimensions of a particularly preferred embodiment of the storage stack 1, storage stack array 8, and a standard microplate (sample container 2). The first lattice constant 9 of the storage stack array 8 (pointing into the X direction of a Cartesian coordinate system) is 99.0 mm. The second lattice constant 10 of the storage stack array 8 (pointing into the Y direction of a Cartesian coordinate system) is 141.5 mm. The outermost dimension of the insulation cover 15 (without resilient circumferential seal 25) in the X and Y direction is 98.0 mm×140.5 mm. The standard microplate measures 85.48 mm×127.76 mm in the X and Y direction. It is amazing to note how little space is necessary and left for the rigid lateral support flanges 11',11" and the rigid back panel 13 of the storage stack 1 according to the invention. In consequence, packing density of the storage stacks 1 is considerably increased when compared to all storage systems that are known from prior art.

Preferably, a storage stack array 8 comprises n×m (e.g. 10×12) storage stacks 1. It is especially preferred that the first lattice constant 9 in the X direction is be-tween 110% and 120% of the width of a microplate according to SBS standards and that the second lattice constant 10 in the Y direction is between 105% and 115% of the length of a microplate according to SBS standards. It is even more preferred that the first lattice constant 9 in the X direction is 115.8% of the width of a microplate according to SBS standards and that the second lattice constant 10 in the Y direction is 110.8% of the length of a microplate according to SBS standards.

FIGS. 4A and 4B show detailed vertical partial sections of an inventive storage stack 1 according to a first variant of the insulation cover 15 that comprises a resilient circumferential seal 25. FIG. 4A shows the rigid insulation cover 15 of the storage stack 1, which comprises a handling plate 16 with a plate circumference surface 17 and an insulation block 18 with a block circumference surface 19.

Also visible is a resilient circumferential seal 25 of the storage stack 1 that preferably is made of resilient polyethylene foam (preferred is a polyethylene foam of the type "J" of Angst & Pfister AG, CH-8052 Zurich, Switzerland) and that, according to carried out experiments, exhibits resilient creeping at temperatures at least down to a temperature of −80° C. According to the respective data sheet, the preferred polyethylene foam type J exhibits fine pores arranged in closed cells. It is chemically neutral (resistant to 30% sulfuric acid, to 10% hydrochloric acid, to sodium hydroxide solution, to fuel oil, to gasoline, to saline water, and limited resistant to chlorinated solvents). It is soft with plane surface, and resistant to age (largely resistant to UV irradiation). Moreover the preferred polyethylene foam type J is exceptionally pliant, practically rot proof, and insensitive to humidity (water absorption is less than 1 vol. %). The raw density (according to DIN 53420) is about 33 kg/m3. It is completely clear of softening agents. The compression rigidity is reported to be about 19 kPA/cm2 (at 10% deformation), about 38 kPA/cm2 (at 25% deformation), and about 105 kPA/cm2 (at 40% deformation).

In this embodiment, the handling plate 16, the insulation block 18 of the insulation cover 15 have the same horizontal overall extension in the X and Y direction. The insulation block 18 comprises a high density polyurethane shell and high density polyurethane stabilizing portions 30. The high density polyurethane shell 29 is filled with a low density polyurethane filling 31. The handling plate 16 and the insulation block 18 of the insulation cover 15 preferably are attached to each other by two screws 36 (not shown here; see FIGS. 6 to 9). Preferably, the handling plate 16 of the insulation block 18 is made of high density polyurethane and connected to the high density polyurethane stabilizing portions 30 of the insulation block 18.

Preferred is high density polyurethane of the type PUR 550 and PUR 900 (handling plate 16 and hd PU shell 29) of Ruhl PUROMER GmbH, DE-61381 Friedrichsdorf, Germany. A preferred 100 g:100 g mixture of these two PUR types exhibits a volumetric weight of 374 kg/m3 (according to DIN EN ISO 845), a shore hardness of 40 Shore D (according to DIN 53505-D), and a tensile strength of 7.3 N/mm2 (according to DIN EN ISO 527).

Preferred is a low density polyurethane of the type PUR 463 RG 48 and PUR 900-1 (ld PU filling 31) of Ruhl PUROMER GmbH, DE-61381 Friedrichsdorf, Germany. A preferred 100 g:130 g mixture of these two PUR types exhibits a volumetric weight of 56 kg/m3 (according to DIN EN ISO 845), a compression strength (d=10%) of 22 N/cm2 (according to DIN 53421).

A metal stabilization plate 34 is molded into the high density polyurethane shell 29 and serves for mechanical stabilization that is preferred for the attachment of the lateral support flanges 11',11" that are linked to the metal stabilization plate 34 by a metal top plate 35. This link is secured by screws 37 that are screw into threaded holes of the metal stabilization plate 34. The metal stabilization plate 34 preferably is made of stainless steel or invar.

The first and second rigid lateral support flanges 11',11" extend in the Z direction and comprise a multitude of storage webs 12. These storage webs 12 serve for supporting sample containers 2 inserted into the storage stack 1. One such sample container 2 (represented by a standard microplate) is inserted in the left storage stack 1 and rests in essentially horizontal position on a pair of these storage webs 12. Other storage webs 12 are subsequently grouped in the Z direction in mutual pairs that protrude about the lateral support flanges and are located thereon on the same Z-level. The storage webs 12, which are bended to extend essentially in the horizontal direction, preferably are partially cut out (or punched out) from the rigid lateral support flanges 11',11" and are still parts of these lateral support flanges 11',11".

Preferably on both sides of the bended-in storage webs 12 but on the outer side of the storage stack 1, the lateral support flanges 11',11" comprise outer vertical corrugations 38 that extend over practically the entire height of the lateral support flanges 11',11". These outer vertical corrugations 38 reduce the surface of contact between two adjacent storage stacks 1 or between a storage stack and the wall structure 33 of the storage area 7 of the low temperature sample store 3 when a storage stack 1 is moved in the Z direction. In addition, these outer vertical corrugations 38 reduce the surface of contact with the plate circumference surface 17 of an adjacent storage stack 1 or of the surrounding rim 32 on the wall structure 33 of the storage area 7 of the low temperature sample store 3 when a storage stack 1 is moved in the Z direction. Alternatively, these outer vertical corrugations 38 reduce the surface of contact with the resilient circumferential seal 25 of an adjacent storage stack 1 or of the surrounding rim 32 on the wall structure 33 of the storage area 7 of the low temperature sample store 3 when a storage stack 1 is moved in the Z direction. The outer vertical corrugations 38 preferably are shifted inwards from the vertical, parallel block circumference 19' by a shifting distance 45 of about 2.2 mm.

Also seen in FIG. 4A is the rigid back panel 13 that rigidly links the lateral support flanges 11',11" to each other. For better circulation of the cold air inside the storage area 7 of the low temperature sample store 3 and particularly in the vicinity of the sample containers 2 that are stored within the storage stacks 1, the rigid back panel 13 comprises cutouts 39. These cutouts 39 also contribute to reducing the overall weight of a storage stack 1.

FIG. 4B shows the rigid bottom plate 14 of the storage stack 1 and carrying pins 27 that are attached to the bottom structure 22 of the storage area 7 of the low temperature sample store 3. Here, the carrying pins 27 are abutted by a metal bottom plate 41 that belongs to the rigid bottom plate 14 of the storage stack 1. The carrying pins 27 actually reach through a hole in the high density polyurethane material of the rigid bottom plate 14 of the storage stack 1. Alternatively, the carrying pins 27 that preferably are connected (e.g. by welding) to the bottom structure of the low temperature sample store 3 are abutted by a plate of hard plastic material that is inserted into the hole in the high density polyurethane material of the rigid bottom plate 14 and that is attached to the metal bottom plate 41 that belongs to the rigid bottom plate 14 of the storage stack 1 (not shown). Utilization of such a hole in the high density polyurethane material of the rigid bottom plate 14 enables the use of longer carrying pins 27 and thus, for minimizing temperature sensitive contact with the surface of the bottom structure 22 of the storage area 7 of the low temperature sample store 3. This rigid bottom plate 14 preferably has, at least partially, a cone-like outer surface that provides a self-centering and guiding function when lowering the storage stack to its bottom storage position 5.

Preferably the handling plate 16, the insulation block 18 of the insulation cover 15, and the bottom plate 14 have the same horizontal overall extension in the X and Y direction.

FIGS. 5A and 5B also shows detailed vertical partial sections of an inventive storage stack 1. It is however different from the FIG. 4 in that it shows a second variant of the insulation cover 15 that defines sealing gaps 23. It also shows an alternative carrying element in the form of a trunnion 21 that is provided with the storage stack 1. FIG. 5A shows the rigid insulation cover 15 of the storage stack 1; the insulation block 18 of this rigid insulation cover 15 having at its upper end a parallel section of the block circumference surface 19 that extends for less than half of the insulating block height. This creates a path length of the gap 23 that is less favorable than depicted in the FIG. 9. Again, the handling plate 16 and the insulation block 18 of the insulation cover 15 have the same horizontal overall extension in the X and Y direction, and the insulation block 18 comprises a high density polyurethane shell 29 and high density polyurethane stabilizing portions 30, the high density polyurethane shell 29 being filled with a low density polyurethane filling 31. As in FIGS. 4A and 4B, the handling plate 16 of the insulation block 18 is made of high density polyurethane and connected to the high density polyurethane stabilizing portions 30 of the insulation block 18.

The left insulation block 18 comprises two fiber reinforced dilatation stabilization portions 44. These reinforced dilatation stabilization portions 44 are embedded inside the insulation block 18 and are located within the region of parallel block circumference surfaces 19 of the insulation cover 15. The fibers for these reinforced dilatation stabilization portions 44 are preferably selected from a group of fibers that comprises glass fibers, carbon fibers, metal fibers, and any combinations thereof. The right insulation block (only partially shown) comprises three fiber reinforced dilatation stabilization portions 44. These reinforced dilatation stabilization portions 44 are embedded inside the insulation block 18 and are located within the parallel region of the block circumference surfaces 19 of the insulation cover 15. It is thus contemplated to utilize a different number of reinforced dilatation stabilization portions 44 according to the intended path length of the gap 23 between two adjacent insulation covers 15 or between an insulated cover 15 and the surrounding rim 32 of the low temperature sample store 3. Also one single reinforced dilatation stabilization portion 44, but with extended thickness (in Z direction) is feasible.

FIG. 5B shows the rigid bottom plate 14 of the storage stack 1 and a trunnion 21 that is attached to the metal bottom plate 41 of the storage stack 1. The trunnion 21 actually reaches through a hole in the high density polyurethane material of the rigid bottom plate 14 of the storage stack 1. Alternatively, the trunnion 21, which preferably is screwed to the to the metal bottom plate 41 here, is attached (e.g. by gluing) to a plate of hard plastic material that is inserted into the hole in the high density polyurethane material of the rigid bottom plate 14 and that is attached to the metal bottom plate 41 (not shown).

Deviating from the presentations in the FIGS. 4A and 4B and FIGS. 5A and 5B, but still within the gist of the disclosed embodiment, there can be a combination of trunnion(s) 21 and carrying pin(s) 27, the number of the trunnion(s) 21 and carrying pin(s) 27 being one or more.

In FIGS. 5A and 5B as well as in FIGS. 4A and 4B inner vertical corrugations 40 are visible on the back panel 13. These inner vertical corrugations 40 run on both sides of the cutouts in the back panel 13 and provide a small rear abutting surface for the sample containers 2 that are inserted into the storage stack 1 by an arm 28 of the robot 4 of the low temperature sample store 3.

It is to be expressly noted here that expansion coefficient of the materials used for the insulation cover 15, the surrounding rim 32, and the wall structure 33 of the storage area 7 of the low temperature sample store 3 are very important when utilizing the variant according to the embodiment of the insulation cover 15 without a circumferential resilient seal 25 but with gaps 23 between the insulating covers 15 of the storage stacks 1 and between the storage stacks 1 and the surrounding rim 32 of the low temperature sample store 3. The use of reinforced dilatation stabilization portions 44 is made with respect to reducing the expansion coefficient of the insulation covers 15.

It has been detected by the present inventors that the wall structure 33 of the storage area 7 of the low temperature sample store 3 and the surrounding rim 32 exhibit an expansion coefficient of 20-23 pm/mK (micrometer per meter and Kelvin). Further investigations revealed that the expansion coefficient of the polyurethane material used for the insulating covers 15 is about 60-70 pm/mK. With the help of the reinforced dilatation stabilization portions 44, the expansion coefficient of the polyurethane material used for the insulating covers 15 is proposed to be lowered to about less than double the expansion coefficient of the wall structure 33 of the storage area 7 of the low temperature sample store 3 and the surrounding rim 32, i.e. to less than 40-46 pm/mK. Limiting the expansion constant of the polyurethane material used for the insulating covers 15 avoids increased leakage of air between the storage area 7 and the transfer area 26 above the storage area 7 of the low temperature sample store 3. In addition, a material and structural combination is used for the insulating cover 15, this combination showing an expansion coefficient that is at least higher than the expansion coefficient of the wall structure 33 of the storage area 7. In consequence, blockage of the storage stacks 1 of the storage array 8 that is kept inside of the storage area 7 of a low temperature sample store 3 is avoided.

The FIG. 6 shows a 3D view of an entire storage stack 1 according to a first variant of the insulation cover 15 of the inventive storage stack 1. This insulation cover 15 comprises a resilient circumferential seal 25. On top of the storage stack 1 is the handling plate 16. This handling plate 16 comprises a handling opening 42 and a handling depression 43 for safe gripping the storage stack 1 by a gripper (not shown) of the robot 4 in the transfer area 26 of a low temperature sample store 3. Also visible on this FIG. 6 are the two screws 36 that fix the handling plate 16 to the rigid insulation cover 15 of the storage stack 1. For description of the other indicated features see the description of FIGS. 4A and 4B.

The FIG. 7 shows a 3D view of an entire storage stack 1 according to a second variant of the insulation cover 15 of the inventive storage stack 1. This insulation cover 15 defines sealing gaps 23 on all of its sides, i.e. about all its vertical, parallel region of the block circumference surfaces 19. Here, the path length of the resulting gap 23 is less favorable than depicted in the FIG. 9 (compare with FIG. 5A), because the vertical, parallel portion of the block circumference surfaces 19 is only about a fourth to the inclined portion of the block circumference surfaces 19.

Figure 8:
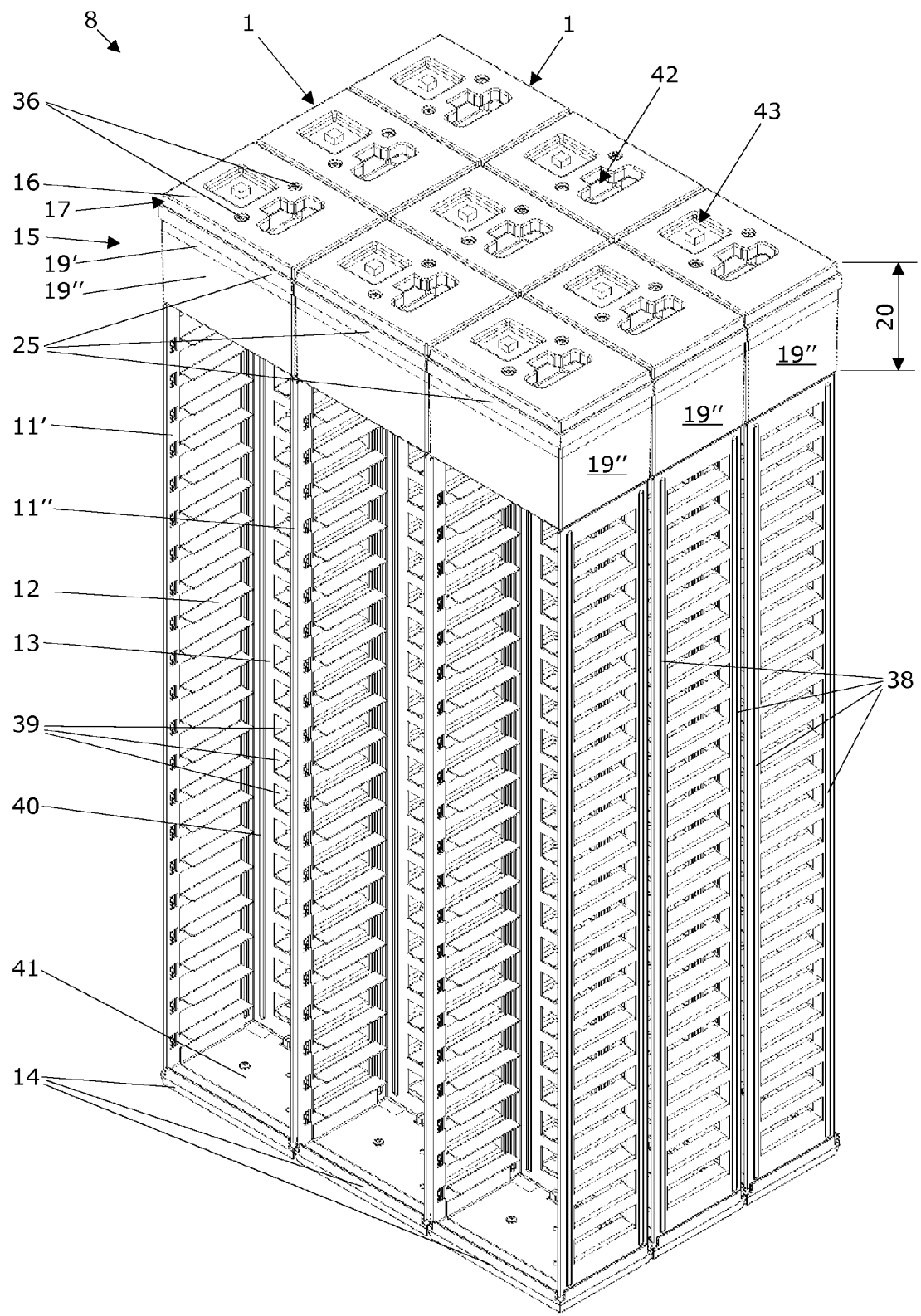
FIG. 8 shows a 3D view of a storage stack array according to a first variant of the insulation cover that comprises a resilient circumferential seal.

FIG. 8 shows a 3D view of a 3×3 storage stack array 8 according to a first variant of the insulation cover 15 of the inventive storage stack 1. This insulation cove 15 comprises a resilient circumferential seal 25. All what has been said in connection with the FIGS. 4A and 4B and 6 also applies here.

Figure 9:
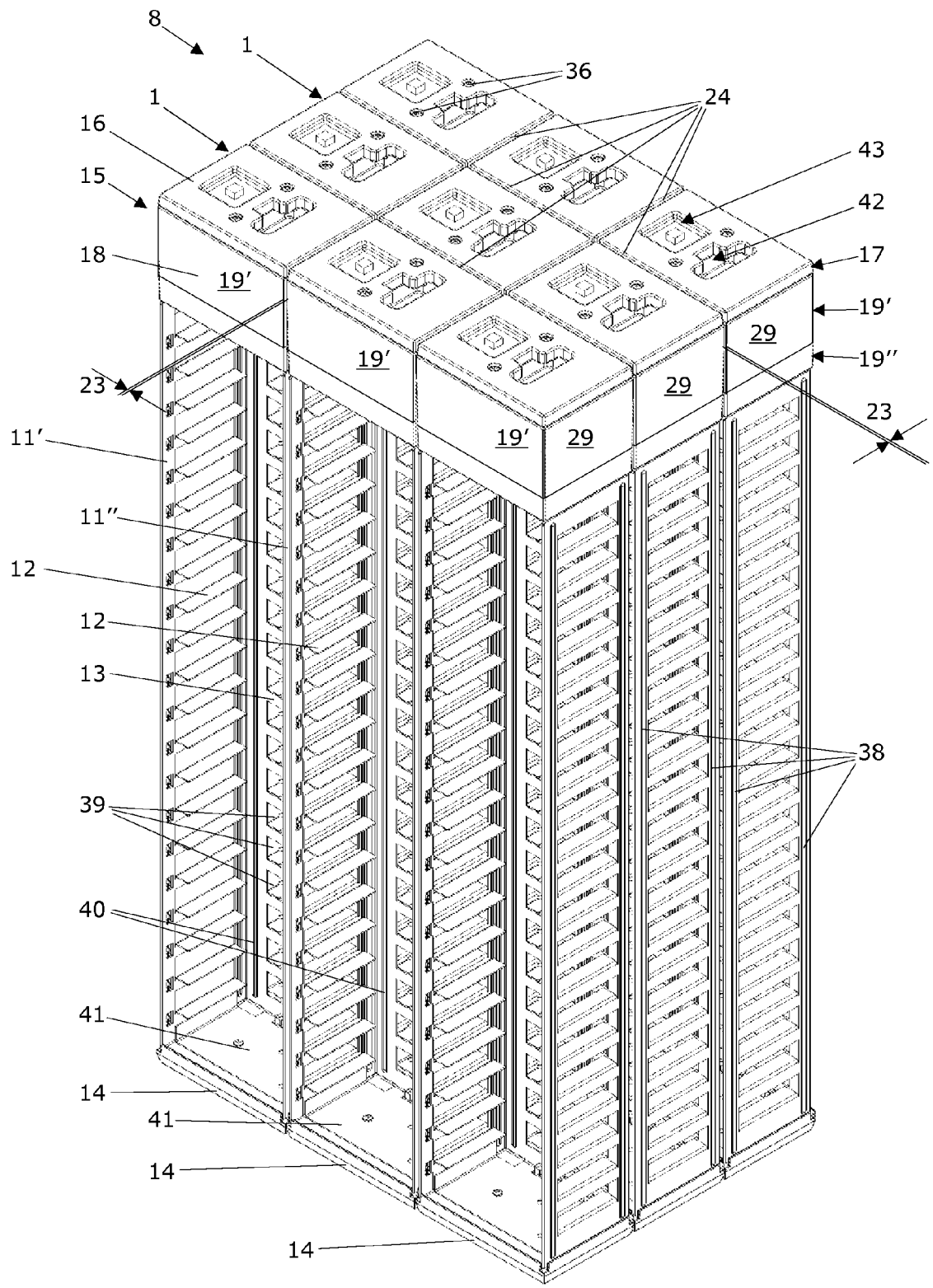
FIG. 9 shows a 3D view of a storage stack array according to a second variant of the insulation cover that defines sealing gaps.

FIG. 9 shows a 3D view of a 3×3 storage stack array 8 according to a second variant of the insulation cover 15 of the inventive storage stack 1. This insulation cover 15 defines sealing gaps 23. All what has been said in connection with the FIGS. 5A and 5B and 7 also applies here. However, this FIG. 9 shows a particularly preferred embodiment of the second variant of the insulation cover 15: This insulation cover 15 defines sealing gaps 23 on all of its sides, i.e. about all its vertical, parallel region of the block circumference surfaces 19. Here, the path length of the resulting gap 23 is most favorable, because the vertical, parallel portion of the block circumference surfaces 19 is about 75% and the inclined portion of the block circumference surfaces 19 is about 25% of the height of the insulating block 18.

In an insulating method for thermal separation of a storage area 7 and a transfer area 26 in a low temperature sample store 3, the method comprises:

(a) providing a storage area 7 that comprises m first lattice constants 9 of an orthogonal lattice in the horizontal X direction and n second lattice constants (10) of said orthogonal lattice in the horizontal Y direction; and (b) providing and arranging a number of m×n storage stacks 1 according to aspects of the disclosed embodiment.

The insulating method according to aspects of the disclosed embodiment is characterized in that a resilient circumferential seal 25 of each storage stack 1 that partially protrudes on all sides beyond the circumference surfaces 17,19 of the handling plate 16 and insulation block 18 of the insulation cover 15 is compressed in the X direction to a dimension that is equal to the first lattice constant 9 of said orthogonal lattice and compressed in the Y direction to a dimension that is equal to the second lattice constant 10 of said orthogonal lattice.

An inventive use of a resilient polymer foam material is proposed. This use of a resilient polymer foam material is applied for sealing thermal separation of a storage area 7 and a transfer area 26 in a low temperature sample store 3. The following is provided for carrying out the use:

(a) a storage area 7 that comprises m first lattice constants 9 of an orthogonal lattice in the horizontal X direction and n second lattice constants 10 of said orthogonal lattice in the horizontal Y direction;

(b) a number of m×n storage stacks 1 according to the disclosed embodiment and arranged in a storage stack array 8.

The inventive use is characterized in that a resilient circumferential seal 25 of each storage stack 1 that partially protrudes on all sides beyond the circumference surfaces 17,19 of the handling plate 16 and insulation block 18 of the insulation cover 15 is produced from polyethylene foam.

The resilient circumferential seal 25 is preferably made of resilient polyethylene foam that exhibits creeping at temperatures at least down to a temperature of −80° C.

An aspect of the disclosed embodiment is to provide alternative storage stacks for storing sample containers in a low temperature sample store.

This aspect is achieved by a storage stack for storing sample containers in a low temperature sample store with the features of the independent claim 1. The low temperature sample store preferably is equipped with a robot, the robot acting according to Cartesian X, Y, and Z coordinates for horizontally positioning sample containers in X/Y planes inside of individual storage stacks and for vertically moving individual storage stacks within the low temperature sample store in Z direction between a bottom storage position and elevated access positions. The sample store preferably defines a storage area for accommodating an array of storage stacks, which storage area comprises m first lattice constants of an orthogonal lattice in the horizontal X direction and n second lattice constants of said orthogonal lattice in the horizontal Y direction. The m×n storage stacks of the storage stack array are all accomplished to be oriented adjacent to each other and parallel to the vertical Z direction.

Each storage stack according to aspects of the disclosed embodiment is characterized in that it includes:

(a) first and second rigid lateral support flanges extending in the Z direction and comprising a multitude of storage webs for supporting sample containers inserted into the storage stack; said storage webs being subsequently grouped in the Z direction in mutual pairs that protrude about the lateral support flanges and that are located thereon on the same Z-level;

(b) a rigid back panel, rigidly linking the lateral support flanges to each other;

(c) a rigid bottom plate, fixed to lower ends of at least one lateral support flange and/or of the back panel; and (d) a rigid insulation cover, fixed to upper ends of at least one lateral support flange and/or of the back panel, the insulation cover comprising:

(i) a handling plate with a plate circumference surface, and (ii) an insulation block with a block circumference surface.

Each storage stack according to aspects of the disclosed embodiment is further characterized in that the m×n insulation covers of all storage stacks of the storage stack array form an essentially continuous insulation layer on the storage area of the low temperature sample store.

Each storage stack according to aspects of the disclosed embodiment is also characterized in that carrying elements are provided, which carrying elements 21,27 statically connect the bottom plate of each individual storage stack with a bottom structure of the storage area of the low temperature sample store, these carrying elements being accomplished to carry the entire weight of the individual storage stack and all sample containers inserted in this storage stack (1) and to confer this entire weight to the bottom structure of the storage area of the low temperature sample store.

One aspect of the storage stack according to the disclosed embodiment, the carrying element of an individual storage stack is accomplished as one or more trunnions, said trunnions being attached to the rigid bottom plate of the storage stack and abutting the bottom structure of the storage area of the low temperature sample store when the individual storage stack is in its bottom storage position.

In another aspect of the storage stack according to the disclosed embodiment, the carrying element of an individual storage stack is accomplished as one or more carrying pins, said carrying pins being attached to the bottom structure of the storage area of the low temperature sample store and being abutted by the bottom plate of an individual storage stack when lowered to its bottom storage position.

In addition other aspects of the storage stack according to the disclosed embodiment may be provided such as, e.g., a combination of trunnions and carrying pins for carrying a single individual storage stack is contemplated as well. In this case, the trunnions and carrying pins can be made of smaller dimensions, because the same weight is distributed to more carrying members.

Additional features according to aspects of the disclosed embodiment are described above.

Advantages of a storage stack according to aspects of the disclosed embodiment include:

1. The storage stacks provide the entire essentially continuous insulation layer on top of the storage area of the low temperature sample store. Thus, a separate insulating ceiling plate as known from U.S. Pat. No. 6,694,767 B2 is unnecessary.

2. The storage stacks individually stand on the bottom structure of the storage area of the low temperature sample store. Again, a separate insulating ceiling plate for carrying the weight of the stacks and sample containers as known from U.S. Pat. No. 6,694,767 B2 is unnecessary.

3. The packing density of the storage stacks is increased, because the insulation covers of the storage stacks are only minimal larger in their horizontal X/Y extension than the sample containers that preferably have the size of Microplates according to the ANSI/SBS 1-2004 standard.

4. The storage stacks are self-centering and self guiding. Thus, guiding grids as disclosed in the priority document to this application are unnecessary.

5. The storage area of the low temperature sample store preferably is devoid of any guidance members for the storage stacks and also devoid of any supporting members for the insulation covers of the storage stacks. Thus, the inventive storage stacks provide for simpler low temperature sample store construction.

The absence of guiding members for the storage stacks, which is a preferred feature according to this invention, allows for easier circulation of air between the storage stacks. Thus, an evenly distributed temperature profile throughout the entire storage area is achieved.

When combining the advantages 1, 2, 4, and 5 as listed above, the use of storage stacks according to this invention offers the opportunity to accommodate the storage system for use in applications where the use of a 1st and/or 2nd lattice constant is preferably and essentially different from the 1st and/or 2nd lattice constant described in this disclosure without the need of design change of the storage area. Thus, design flexibility for low temperature storage systems is provided to a greater extent than known from prior art.

The same reference numbers in the Figures relate to the same features even when not in every case each reference number is carefully addressed in the specification. Reasonable combinations of the described and/or shown embodiments and variants belong to the disclosed embodiment.

REFERENCE NUMBERS 1 storage stack
2 sample container
3 low temperature sample store
4 robot
5 bottom storage position
6 elevated access position
7 storage area
8 storage stack array
9 first lattice constant
10 second lattice constant
11' first rigid lateral support flange
11" second rigid lateral support flange
12 storage web
13 rigid back panel
14 rigid bottom plate
15 rigid insulation cover
16 handling plate of 15
17 plate circumference surface
18 insulation block of 15
19' vertical, parallel block circumference surface
19" inclined block circumference surface
20 essentially continuous insulation layer
21 trunnion
22 bottom structure of 7
23 sealing gap
23' first gap part
23" second gap part
24 gap array
25 circumferential resilient seal
26 transfer area
27 carrying pin
28 arm of the robot
29 hd PU shell
30 hd PU stabilizing portion
31 ld PU filling
32 surrounding rim
33 wall structure of storage area
34 metal stabilization plate
35 metal top plate
36 screws
37 screws
38 outer vertical corrugations
39 cutouts in 13
40 inner vertical corrugations
41 metal bottom plate
42 handling opening
43 handling depression
44 reinforced dilatation stabilization portions
45 shifting distance

The invention claimed is:

1. A storage stack for storing sample containers in a low temperature sample store equipped with a robot, the robot acting according to Cartesian X, Y, and Z coordinates for horizontally positioning sample containers in X/Y planes inside of individual storage stacks and for vertically moving individual storage stacks within the low temperature sample store in Z direction between a bottom storage position and elevated access positions; the sample store including a surrounding rim that defines a storage area having a common opening for accommodating an array of storage stacks, the storage area comprising m first lattice constants of an orthogonal lattice in the horizontal X direction and n second lattice constants of said orthogonal lattice in the horizontal Y direction; the m×n storage stacks of the storage stack array being accomplished to be oriented adjacent to each other and parallel to the vertical Z direction,
  wherein each individual storage stack comprises:
    (a) first and second rigid lateral support flanges extending in the Z direction and comprising a multitude of storage webs for supporting sample containers inserted into the storage stack; said storage webs being subsequently grouped in the Z direction in mutual pairs that protrude about the lateral support flanges and that are located thereon on the same Z-level;
    (b) a rigid back panel, rigidly linking the lateral support flanges to each other;
    (c) a rigid bottom plate, fixed to lower ends of at least one lateral support flange and/or of the back panel; and
    (d) a rigid insulation cover, fixed to upper ends of at least one lateral support flange and/or of the back panel, the insulation cover comprising:
      (i) a handling plate with a plate circumference surface, and
      (ii) an insulation block with a block circumference surface; wherein the m×n insulation covers of all storage stacks of the storage stack array form an essentially continuous insulation layer, independent of the surrounding rim, on the common opening of the storage area of the low temperature sample store;
    and wherein carrying elements are provided, which carrying elements statically connect the bottom plate of each individual storage stack with a bottom structure of the storage area of the low temperature sample store, these carrying elements being accomplished to carry the entire weight of the individual storage stack and all sample containers inserted in this storage stack and to confer this entire weight to the bottom structure of the storage area of the low temperature sample store.

2. The storage stack of claim 1, wherein the carrying element of an individual storage stack is accomplished as one or more trunnions, said trunnions being attached to the rigid bottom plate of the storage stack and abutting the bottom structure of the storage area of the low temperature sample store when the individual storage stack is in its bottom storage position.

3. The storage stack of claim 1, wherein the carrying element of an individual storage stack is accomplished as one or more carrying pins, said carrying pins being attached to the bottom structure of the storage area of the low temperature sample store and being abutted by the bottom plate of an individual storage stack when lowered to its bottom storage position.

4. The storage stack of claim 1, wherein the handling plate and the insulation block of the insulation cover have a horizontal overall extension in the X and Y direction that is greater than 95% of the first and second lattice constants of said orthogonal lattice.

5. The storage stack of claim 1, wherein the handling plate and the insulation block of the insulation cover have a horizontal overall extension in the X and Y direction that is equal or greater than 99% of the first and second lattice constants of said orthogonal lattice.

6. The storage stack of claim 1, wherein the handling plate and the insulation block of the insulation cover have a horizontal overall extension in the X direction that is less than 2% smaller than the first lattice constant and that is less than 1.4% smaller than the second lattice constant in the Y direction of said orthogonal lattice.

7. The storage stack of claim 6, wherein the handling plate and the insulation block of the insulation cover define first gap parts of 0.5% of the first lattice constant in the X direction and second gap parts of 0.35% of the second lattice constant in the Y direction of said orthogonal lattice.

8. The storage stack of claim 7, wherein the gap parts form a gap array that is coincident with said orthogonal lattice.

9. The storage stack of one claim 1, wherein the handling plate and the insulation block of the insulation cover have a horizontal overall extension in the X direction that is 1% smaller than the first lattice constant and that is 0.7% smaller than the second lattice constant in the Y direction of said orthogonal lattice.

10. The storage stack of claim 1, wherein the insulation cover further comprises:
(iii) a resilient circumferential seal partially located between the handling plate and the insulation block;
and wherein the resilient circumferential seal of a single storage stack partially protrudes on all sides beyond the circumference surfaces of the handling plate and insulation block and extends beyond the first lattice constant in the X direction and beyond the a second lattice constant in the Y direction of said orthogonal lattice.

11. The storage stack of claim 10, wherein the resilient circumferential seal of a single storage stack protrudes about more than 0.2% beyond the lattice constants in the X direction and in the Y direction of said orthogonal lattice.

12. The storage stack of claim 10, wherein the resilient circumferential seal of a single storage stack protrudes at +25° C. about 0.75% and at −80° C. about 0.35% beyond the lattice constants in the X direction and in the Y direction of said orthogonal lattice.

13. The storage stack of claim 10, wherein the resilient circumferential seal is made of a resilient polyethylene foam that exhibits creeping at temperatures at least down to a temperature of −80° C.

14. The storage stack of claim 1, wherein the handling plate, the insulation block of the insulation cover, and the bottom plate have the same horizontal overall extension in the X and Y direction.

15. The storage stack of claim 1, wherein the insulation block comprises a high density polyurethane shell and high density polyurethane stabilizing portions, the high density polyurethane shell being filled with a low density polyurethane filling.

16. The storage stack of claim 15, wherein the handling plate of the insulation block is made of high density polyurethane and connected to the high density polyurethane stabilizing portions of the insulation block.

17. The storage stack of claim 15, wherein the insulation block comprises fiber reinforced dilatation stabilization portions that are embedded inside the insulation block and that are located within the region of parallel block circumference surfaces of the insulation cover.

18. A storage stack array comprising n x m storage stacks according to claim 1, wherein the first lattice constant in the X direction is between 110% and 120% of the width of a microplate according to SBS standards;
and wherein the second lattice constant in the Y direction is between 105% and 115% of the length of a microplate according to SBS standards.

19. The storage stack array of claim 18,
wherein the first lattice constant in the X direction is 115.8% of the width of a microplate according to SBS standards;
and wherein the second lattice constant in the Y direction is 110.8% of the length of a microplate according to SBS standards.

20. An insulating method for thermal separation of a storage area and a transfer area in a low temperature sample store, the method comprising: (a) providing a storage area that comprises m first lattice constants of an orthogonal lattice in the horizontal X direction and n second lattice constants of said orthogonal lattice in the horizontal Y direction; and (b) providing and arranging a number of m×n storage stacks within the common opening according to claim 1;
wherein a resilient circumferential seal of each storage stack that partially protrudes on all sides beyond the circumference surfaces of the handling plate and insulation block of the insulation cover is compressed in the X direction to a dimension that is equal to the first lattice constant of said orthogonal lattice and compressed in the Y direction to a dimension that is equal to the second lattice constant of said orthogonal lattice.

* * * * *